(12) United States Patent
Olcott et al.

(10) Patent No.: US 9,069,089 B2
(45) Date of Patent: Jun. 30, 2015

(54) METHODS AND SYSTEMS FOR INCREASING THE SENSITIVITY OF SIMULTANEOUS MULTI-ISOTOPE POSITRON EMISSION TOMOGRAPHY

(75) Inventors: Peter D. Olcott, Stanford, CA (US); Craig S. Levin, Palo Alto, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 0 days.

(21) Appl. No.: 13/984,074

(22) PCT Filed: Mar. 30, 2012

(86) PCT No.: PCT/US2012/031619
§ 371 (c)(1),
(2), (4) Date: Aug. 7, 2013

(87) PCT Pub. No.: WO2012/135725
PCT Pub. Date: Oct. 4, 2012

(65) Prior Publication Data
US 2014/0008542 A1     Jan. 9, 2014

Related U.S. Application Data

(60) Provisional application No. 61/516,146, filed on Mar. 30, 2011.

(51) Int. Cl.
*G01T 1/20*     (2006.01)
*G01T 1/29*     (2006.01)
(Continued)

(52) U.S. Cl.
CPC ............... *G01T 1/2985* (2013.01); *A61B 6/037* (2013.01); *A61B 6/4241* (2013.01); *A61B 6/4258* (2013.01); *A61B 6/4266* (2013.01); *A61B 6/508* (2013.01); *G01T 1/1647* (2013.01)

(58) Field of Classification Search
CPC ..................................................... G01T 1/2985

USPC ...................................................... 250/363.03
See application file for complete search history.

(56) References Cited

U.S. PATENT DOCUMENTS

| 5,083,026 A | 1/1992 | Elbaum |
| 5,512,754 A | 4/1996 | Enos |

(Continued)

OTHER PUBLICATIONS

Andreyev et al. (2010) entitled "Feasibility study of dual isotope PET", published in Nuclear Science Symposium Conference Record (NSS/MIC), 2010 IEEE (Oct. 30, 2010-Nov. 6, 2010), pp. 2108-2111.

(Continued)

*Primary Examiner* — David Porta
*Assistant Examiner* — Hugh H Maupin
(74) *Attorney, Agent, or Firm* — Lumen Patent Firm (57) ABSTRACT

Positron emission tomography (PET) systems suitable for use with dirty (positron+prompt gamma) emitters are provided. One or more prompt gamma detectors are added to the PET system, where the prompt gamma detectors are responsive to the prompt gammas provided by the dirty emitter, but are not responsive to 511 keV annihilation photons. The prompt gamma detectors can surround the imaging PET detector array and/or be disposed as end caps relative to a generally cylindrical PET detector array. The prompt gamma detectors need not provide spatial resolution, because coincidence events in the PET detector array are classified as 2-photon or 3-photon events depending on whether or not there is a time-coincident signal from the prompt gamma detectors. One application of this approach is dual isotope PET where distinct tracers labeled with clean and dirty positron emitters are simultaneously imaged.

13 Claims, 6 Drawing Sheets

(51) Int. Cl.
    *A61B 6/03*     (2006.01)
    *A61B 6/00*     (2006.01)
    *G01T 1/164*     (2006.01)

(56) References Cited

U.S. PATENT DOCUMENTS

| | | | |
|---|---|---|---|
| 6,480,451 | B2 | 11/2002 | Miyauchi et al. |
| 7,894,652 | B2 | 2/2011 | Casey et al. |
| 2001/0056234 | A1* | 12/2001 | Weinberg ............... 600/436 |
| 2005/0117682 | A1* | 6/2005 | Akers .................... 376/157 |
| 2008/0033291 | A1 | 2/2008 | Rousso et al. |
| 2008/0111081 | A1* | 5/2008 | Chuang .................. 250/363.03 |
| 2008/0283758 | A1 | 11/2008 | Hayden et al. |
| 2009/0057561 | A1 | 3/2009 | Schweizer et al. |
| 2010/0015058 | A1 | 1/2010 | Li |
| 2010/0260673 | A1 | 10/2010 | Cao et al. |
| 2010/0268074 | A1 | 10/2010 | Glodo et al. |

OTHER PUBLICATIONS

Andreyev et al. (2011) entitled Dual-isotope PET using positron-gamma emitters, published in Phys Med Biol. Jul. 21, 2011;56(14):4539-56. Epub Jul. 1, 2011.

* cited by examiner

METHODS AND SYSTEMS FOR INCREASING THE SENSITIVITY OF SIMULTANEOUS MULTI-ISOTOPE POSITRON EMISSION TOMOGRAPHY

FIELD OF THE INVENTION

This invention relates to positron emission tomography (PET).

BACKGROUND

In PET imaging, a positron emitting isotope is disposed within an object being imaged. Typically, the positron emitting isotope is included in a chemical tracer, which is thereby labeled with the isotope. Positrons emitted by the isotope rapidly encounter an electron within the object and annihilate, thereby creating a pair of oppositely directed 511 keV gamma ray photons. Coincidence detection of the 511 keV photons is employed in an imaging detector array to provide spatially resolved imaging of the annihilation events (i.e., the PET image).

Positron emitting isotopes can be roughly divided into so-called "clean" emitters and "dirty" emitters depending on whether or not positron emission is accompanied by other kinds of radioactive emission. For clean emitters, there is relatively little non-positron emission (e.g., 10% or less), while dirty positron emitters can have greater non-positron emission (e.g., more than 10%). Since the non-positron radiation emitted by dirty positron emitters can cause undesirable background noise in a PET system, clean positron emitters are preferred in conventional PET systems. Some attention has been paid to correcting PET imaging results for the presence of background noise from dirty positron emitters, e.g., as considered in U.S. Pat. No. 7,777,189 and in US 2008/0283758.

Some attention has also been paid to exploiting dirty emitters to provide more information from a PET system than can be obtained using conventional clean positron emitters. An example of this approach is described in an article by Andreyev et al. ("Feasibility study of dual-isotope PET", IEEE Nuclear Science Symposium 1020 Conference Record pp 2108-2111). In this work, two isotopes are used simultaneously in PET, where the first isotope is a clean positron emitter, and the second isotope is a dirty positron emitter that provides a prompt gamma ray in addition to a positron. Signals from the two isotopes are distinguished by determining whether a detected event is a 2-photon event (attributed to the clean emitter) or a 3-photon event (attributed to the dirty emitter).

SUMMARY

We have found that satisfactory imaging of 3-photon events (also referred to as triple-coincidence events) can be very difficult in a conventional PET system. The basic reason for this is low detection efficiency. For conventional PET, the detection rate for the 2 annihilation photons is typically about 1-3%. The detection rate for a prompt gamma in a PET system also tends to be quite low, and these two low efficiencies would be multiplied to obtain the detection efficiency of 3-photon events. Low efficiency leads to poor statistics (i.e., reduced signal/noise), which in turn degrades the ability to detect, visualize or quantify the spatial extent and concentration of triple coincidence emitters.

The present work relates to PET systems having configurations for improved detection of 3-photon events, thereby alleviating the above-described problem of low sensitivity, and enabling improved dual isotope PET with clean and dirty emitters simultaneously imaged.

One or more prompt gamma detectors is placed in proximity to the rest of the PET system. The PET system processor is capable of distinguishing between 2-photon events and 3-photon events according to signals provided by the imaging detector array of the PET system (which is responsive to 511 keV photons) and by the prompt gamma detectors (which are responsive to prompt gamma photons, but are not responsive to 511 keV annihilation photons). The prompt gamma detectors need not provide spatial resolution, so large single-element and/or single-channel detectors can be used for the prompt gammas to provide improved prompt gamma detection efficiency without greatly adding to system cost. Note that a naive approach of extending the size/coverage of the PET imaging array to improve detection efficiency for prompt gammas would be much more costly than the present approach.

The present approach provides various significant advantages. By increasing the sensitivity of 3-photon event detection, simultaneous PET imaging of 2-photon and 3-photon emitters can be enabled. This advantageously reduces total imaging time compared to performing two imaging runs in sequence. If two runs are performed in sequence, it would be necessary to wait for the first tracer to clear before starting the second imaging run, so the time savings can be highly significant. Furthermore, such PET imaging may provide rich biochemical information by performing multi-tracer imaging simultaneously with full temporal and spatial registration.

BRIEF DESCRIPTION OF THE DRAWINGS

FIG. 5b shows results from the experiment of FIG. 5a.

DETAILED DESCRIPTION

There are three classes of conventional PET scanners commercially produced to solve various research and clinical goals—small animal systems, whole body clinical systems, and application-specific systems. Suitable geometrical configurations for the prompt gamma detectors tend to differ depending on the type of PET system under consideration. Thus, it will be helpful to consider these configurations separately. General principles of the invention, as well as considerations specific to small animal PET systems are considered in connection with FIGS. 1a-c. Clinical whole-body systems are considered in connection with FIGS. 2a-b. Application specific systems are considered in connection with FIGS. 3a-b.

Figure 1A:
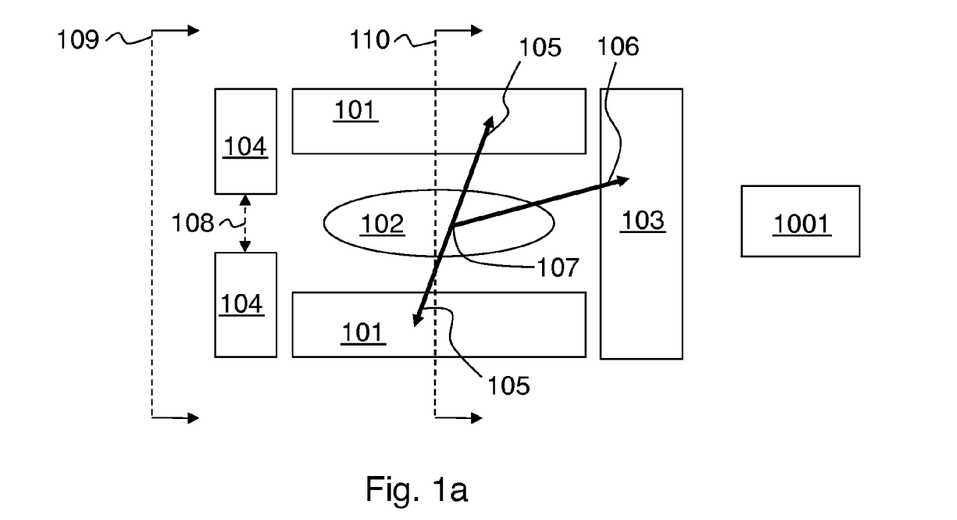
FIGS. 1a-c show a first embodiment of the invention.
Figure 1B:
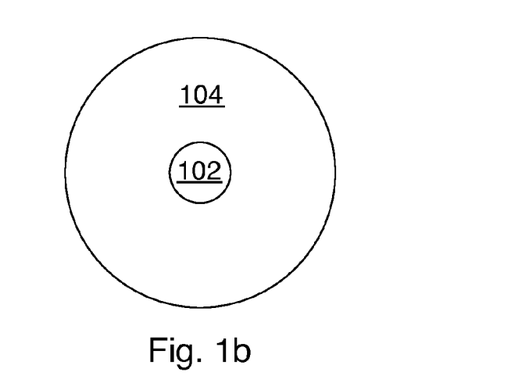
Figure 1C:
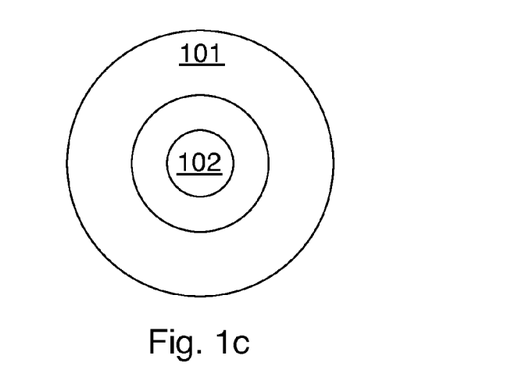

FIGS. 1a-c show a first embodiment of the invention, relating to small animal PET systems. Here FIG. 1b is an end view as seen from line 109 and FIG. 1c is a cross section view as seen from line 110. First, general principles of the invention will be described with reference to FIGS. 1a-c. Then, aspects of the invention that relate to small animal PET systems will be described, also with reference to FIGS. 1a-c.

1) General Principles

The apparatus for radiological imaging of FIGS. 1a-c includes an imaging positron emitting tomography (PET)

detector array 101 capable of detecting and locating two-photon emission events resulting from positron annihilation to provide PET detector signals. Annihilation events occur in object 102 that is being imaged. The apparatus of FIG. 1a also includes one or more prompt gamma detectors 103 and 104, which are responsive to prompt gammas, and are not responsive to positron annihilation photons (at 511 keV). Thus the prompt gamma detectors are capable of improving the detection of a prompt gamma emission from isotopes that produce both a positron and a prompt gamma in cascade. FIG. 1a schematically shows such a 3-photon process, where an event at 107 leads to emission of a prompt gamma 106 and a positron (not shown) which annihilates to provide oppositely directed photons 105.

Typically, prompt gamma detectors 103, 104 are energy selective in order to be responsive to the prompt gammas without being responsive to the 511 keV annihilation photons. Thus, these detectors have an energy window within which they respond, thereby providing energy selectivity. The energy window can be based on the energy resolving capability of the detector. The prompt gamma energy can be greater than 511 keV or less than 511 keV. For a detector with a good energy resolving capability, the selected energy window can be +/−10% of the prompt gamma ray energy. The energy window can also be made wider than +/−10% to improve sensitivity. For example, suppose the prompt gamma has an energy of 800 keV. The above described 10% rule would give an energy window of 720 to 880 keV. The lower end of this window can be decreased (e.g., to 600 keV). A 600-880 keV window will increase the sensitivity of the detector because a Compton interaction that deposits some of the energy of the prompt gamma ray can be as or more likely than ionization that deposits all of the energy of the prompt gamma ray. Thus, it can be helpful to decrease the lower limit of the energy window (while continuing to exclude 511 keV from the window) because some detection events for the prompt gamma will not have the full energy of the prompt gamma. The preceding examples relate to use of an energy window for providing responsiveness to prompt gammas and non-responsiveness to 511 keV annihilation photons. Any other method for providing this selective response capability can also be employed.

Another non-limiting example of a method to determine if a gamma photon is prompt is to use a time window. Because the approximate location of an annihilation event is known by the time-of-flight of the 511 keV annihilation photons, then correspondingly, the time of flight of the gamma can be calculated. If the third gamma is within an acceptable time of flight from the annihilation location, then this can be used to determine whether or not the third gamma is prompt.

A processor 1001 is coupled to the imaging PET detector array 101 and to the prompt gamma detectors 103, 104 (processor connections not shown) and is capable of classifying the PET detector signals as 2-photon events or as 3-photon events according to signals provided by the PET detector array 101 and by the prompt gamma detectors 103, 104. For example, PET analysis of the signals from detector array 101 can provide a list of positron annihilation events. Each of these annihilation events can be classified as a 2-photon event or as a 3-photon event according to the absence or presence, respectively, of a third coincident detector signal from the prompt gamma detectors 103, 104 or from the PET detector array 101. In either case, detection of the prompt gamma ray does not need to be spatially localized. The localization of the positron decay is done by the localization of the two annihilation photons 105 based on energy discrimination and time discrimination.

In most cases, it is preferred for PET detector array 101 to laterally enclose the object being imaged. In other words, the PET detector array has generally the configuration of the side surface of a cylinder that is disposed around the object being imaged. It is also preferred for the PET detector array to provide a spatial resolution substantially more precise than the size of the PET detector array. Methods for accomplishing this are well known in the art relating to PET. Any and all such methods are applicable here.

As indicated above, it is preferred for the prompt gamma detectors to not provide a spatial resolution more Precise than their size. This configuration is preferred to minimize the added cost of the prompt gamma detectors. Of course, prompt gamma detectors providing spatial resolution more precise than their size can be employed, but that would increase cost without providing any significant benefit.

As previously described, 2-photon and 3-photon events are distinguished by the absence or presence of a third detector signal that is coincident with a 2 photon coincidence event as recorded in PET detector array 101. A timing window is employed to determine whether or not such a coincidence has occurred, since exact coincidence is not expected in practice. These timing considerations also affect the desired properties of the prompt gamma emitters. Even though these timing considerations tend to differ for the various PET system configuration, it will be convenient to consider all cases here.

For whole body systems, let w be the patient width, and let c be the speed of light. Then we define $\tau = w/c$. Preferably, the triple-coincidence isotope has a time difference T between positron emission and prompt gamma emission such that T is less than about $\tau$. Note that the prompt gamma can be emitted before or after the positron, so T is by convention defined as a positive quantity (i.e., $T = |t_{pos} - t_{gam}|$, for a prompt gamma emitted at time $t_{gam}$ and a positron emitted at $t_{pos}$). For this case, the coincidence window for defining 3-photon events is preferably in a range from 0 to W, where W is between about $\tau$ and about $3\tau$.

For small animal and application-specific systems, let $T_{FWHM}$ be the detector time response full width half-maximum. Preferably, the triple-coincidence isotope has a time difference T between positron emission and prompt gamma emission such that T is less than about $2T_{FWHM}$. For this case, the coincidence window for defining 3-photon events is preferably in a range from 0 to W, where W is about $2T_{FWHM}$.

In some cases, such as low-count rate situations (as often encountered in small animal or application specific PET), it may be helpful to increase the above-described window ranges and isotope time differences (by as much as a factor of 10×). This can help increase the signal. A prompt gamma emitter is regarded as being any isotope that provides a time difference T between positron emission and prompt gamma emission as described above.

Low-count rate situations can arise where the tracer contrast is extremely high, or the volume of interest as compared to a human is very small. In cases where the contrast is high, then only small numbers of counts are needed to detect the accumulation of the radio tracer. In cases where the volume of interest is very small, then there are very few background processes. Because the background processes are not present, then the window ranges can be relaxed. These low-count situations can occur when attempting to image either small animals such as mice or chemical assays being conducted in small well plates.

Practice of the invention does not depend critically on specific details of the prompt gamma detector design. Any prompt gamma detector consistent with the above-described principles can be employed. In one example, the scintillation crystal used in the prompt gamma ray detectors can be made from $Bi_4Ge_3O_{12}$ (BGO). BGO has a high stopping power for gamma rays above 511 keV and an acceptable decay time of 300 ns. For higher count rate applications, $Lu_2SiO_6$:Ce (LSO) may be used as the prompt gamma ray detector because its decay constant is 40 ns. Other cerium activated scintillation crystals can also be employed. One of the problems of LSO is its natural radioactivity, but for high-energy gamma emitters>900 keV there is little overlap with the energy of this natural radioactivity. Other high energy stopping power scintillators such as $CdWO_4$ may be considered if count rate limitations are not very important.

It will be appreciated by one skilled in the art that many different types of scintillation crystals or solid state high energy photon detectors, such as Cadmium-Zinc-Telluride (CZT), or gas detectors can be used for the detectors to balance the requirements to obtain an adequate energy resolution, timing resolution, cost and stopping power. These detectors can be energy gated for detecting the prompt gamma ray or rays emitted simultaneously with a positron emission (and subsequent annihilation photons).

2) Small Animal Pet Example

Small animal PET research imaging systems are designed to address research questions in small laboratory animals. These systems typically have much smaller diameters (8 cm-15 cm) compared to clinical PET systems, and usually also have a smaller axial extent (4 cm-12 cm). An example is the Siemens Inveon® small animal PET scanner.

In an example of a small animal imaging PET system shown on FIGS. 1a-c, one or more non-spatially encoding prompt gamma ray detector(s) (103 and/or 104) can be operated in coincidence with the cylindrical ring of imaging detectors 101. In this example, the prompt gamma ray detector 103 can be made of a single large cylindrical crystal of approximately 8 cm in diameter and 5 or more cm in thickness. If a single large diameter crystal is not available, the cylindrical crystal can be composed of smaller crystals that are tiled and optically cemented together to form a large diameter cylindrical crystal. A single photomultiplier tube (PMT) can be connected to the large diameter cylindrical scintillation crystal. In another example, solid-state photomultipliers (SiPM) or Avalanche photodiodes (APD) can also be connected to the scintillation crystal of the non-spatially encoding detector(s). Standard scintillation processing electronics including an energy discrimination function and a timing gate can be connected to the output of the prompt gamma photo-detector. In another example, the prompt gamma ray detectors can be made of rectangular individual crystals that are packed together to make a larger detector. The small detection area per detector can help increase the count rate of the prompt gamma detector if pulse pileup is a problem that causes system saturation. The prompt gamma can also be a radiation detector based on either a semiconductor crystal or a gas.

There are many potential configurations for the geometry and placement of the prompt gamma detector. In one example, a cylindrical prompt gamma ray detector 103 can be inserted at one end of the bore of a small animal PET scanner 101 with a live animal 102 placed at the center of the conventional PET detector ring. In another example, another cylindrical prompt gamma detector 104 can be placed on the opposing end, flanking the small animal (i.e., longitudinally enclosing it) to further increase the sensitivity of detecting the prompt gamma ray. In a further example, a port 108 (or multiple ports) for feeding anesthesia, allowing passage of mechanical structures to hold the bed, etc. may be placed in the prompt gamma ray detector.

3) Whole Body Pet Example

Figure 2A:
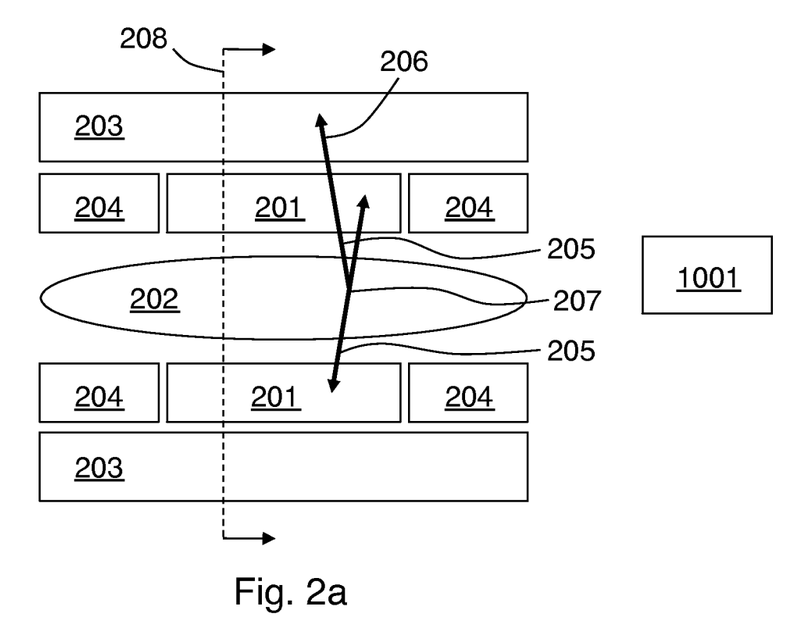
FIGS. 2a-b show a second embodiment of the invention.
Figure 2B:
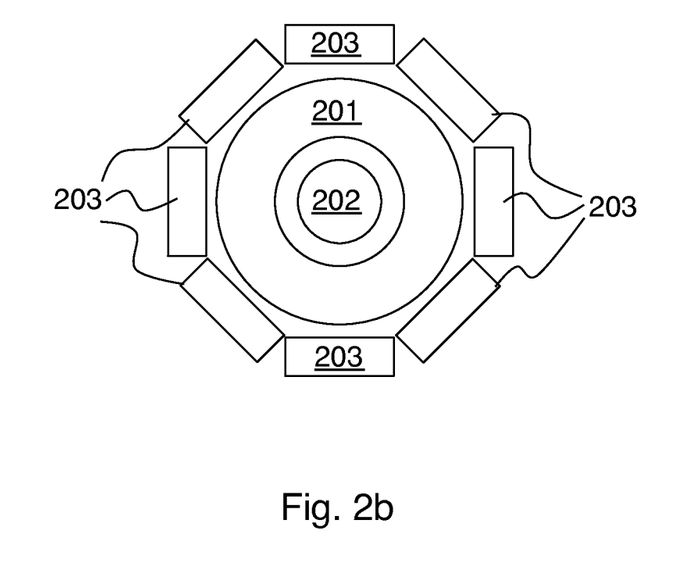

FIGS. 2a-b show a second embodiment of the invention, relating to whole-body clinical PET systems. Here FIG. 2b is a cross section view as seen from line 208. Whole body clinical systems usually have large diameter (60-80 cm) rings with axial extents of approximately 15-20 cm. In one popular clinical configuration, know as "PET/CT" an X-ray computed tomography (CT) machine is integrated with the conventional PET scanner, and the combined system is capable of distinct PET and CT studies of the whole body. PET provides the functional information of a radiotracer and the CT scanner provides information on the structural anatomy of the body.

The apparatus for radiological imaging of FIGS. 2a-b includes an imaging positron emitting tomography (PET) detector array 201 capable of detecting and locating two-photon emission events resulting from positron annihilation to provide PET detector signals. Annihilation events occur in object 202 that is being imaged (e.g., a patient). The apparatus of FIG. 2a also includes one or more prompt gamma detectors 203, which are responsive to prompt gammas, and are not responsive to positron annihilation photons (at 511 keV). Thus the prompt gamma detectors are capable of improving the detection of a prompt gamma emission from isotopes that produce both a positron and a prompt gamma in cascade. FIG. 2a schematically shows such a 3-photon process, where an event at 207 leads to emission of a prompt gamma 206 and a positron (not shown) which annihilates to provide oppositely directed photons 205.

Because of geometrical constraints of the patient 202, the single or dual cylindrical crystal design may not be feasible in whole body clinical PET imaging systems. In the example of FIGS. 2a-b, one or more large rectangular or trapezoidal scintillation crystal(s) 203 can be provided, with a total length that extends beyond the length of the standard PET system detectors. The example of FIGS. 2a-b shows rectangular prompt gamma detectors 203. These extra detector add-ons can be placed as sections around the clinical PET detector array 201. Each large prompt third gamma detector includes a photo-detector and readout electronics in the case of scintillation detectors or just readout electronics in the case of the solid-state detectors. The prompt gamma detector has a much larger size than the small crystals of the conventional clinical PET detector 201. Therefore, with this design, the cost and complexity of adding a prompt third gamma ray detector is greatly reduced as compared to adding more conventional clinical PET detectors to detect the third gamma ray. The detector add-on(s) can be formed into a wide range of geometries that maximize solid angle coverage, while at the same time minimizing the cost. It can be appreciated that these geometries may be trapezoidal, circular, and/or rectangular based on the physical properties of the crystal and practical mechanical requirements, such as to physically attach a photo-detector to a scintillation crystal.

Usually, since the radiation of the prompt gamma ray 206 is at much higher energy than the 511 keV of the annihilation photons 205 from annihilation event 207, it will penetrate the detector array 201 of the conventional PET ring and the associated photo-detector and readout electronics, and with some attenuation, be likely to stop in the large prompt gamma detectors 203 that are placed outside the conventional PET detector. In this example, the prompt gamma detectors include one or more prompt gamma detectors disposed laterally around the PET detector array.

Optionally, including shielding 204 for triple coincidence can help reduce random coincidences from prompt gamma rays that are not from the imaging field of view. The materials used for such a shield 204 can include lead or tungsten to provide high stopping power. Using these shields 204, the prompt gamma rays can be physically collimated to reduce random coincidences.

4) Application Specific Pet Example

Figure 3A:
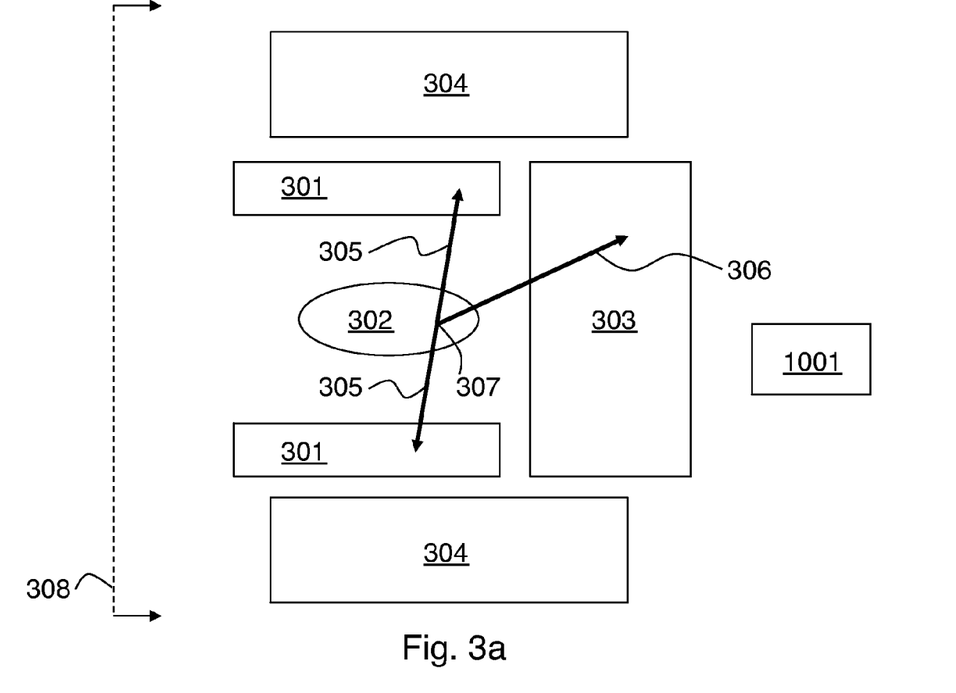
FIGS. 3a-b show a third embodiment of the invention.
Figure 3B:
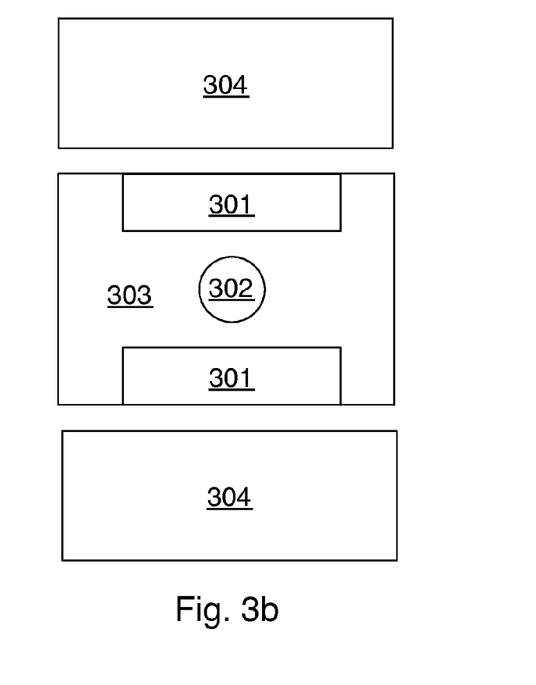

FIGS. 3a-b show a third embodiment of the invention relating to application specific PET systems. In application specific clinical PET scanners, a single organ or limited region is placed between two PET detector arrays that are typically much smaller than whole body clinical PET detector arrays. Higher resolution and sensitivity is achieved, but with the drawback of being limited to imaging only one organ or region of the body. For example, the Naviscan® PET system (from vendor Naviscan, Inc.) is an application specific PET imager for the staging and management of breast cancer.

Here FIG. 3b is an end view as seen from line 308. The apparatus for radiological imaging of FIGS. 3a-b includes an imaging positron emitting tomography (PET) detector array 301 capable of detecting and locating two-photon emission events resulting from positron annihilation to provide PET detector signals. Annihilation events occur in object 302 that is being imaged (e.g., part of a patient). The apparatus of FIG. 3a also includes one or more prompt gamma detectors 303 (front detector) and 304 (side detectors), which are responsive to prompt gammas, and are not responsive to positron annihilation photons (at 511 keV). Thus the prompt gamma detectors are capable of improving the detection of a prompt gamma emission from isotopes that produce both a positron and a prompt gamma in cascade. FIG. 3a schematically shows such a 3-photon process, where an event at 307 leads to emission of a prompt gamma 306 and a positron (not shown) which annihilates to provide oppositely directed photons 305.

5) Whole Body Pet

Second Example

Figure 4A:
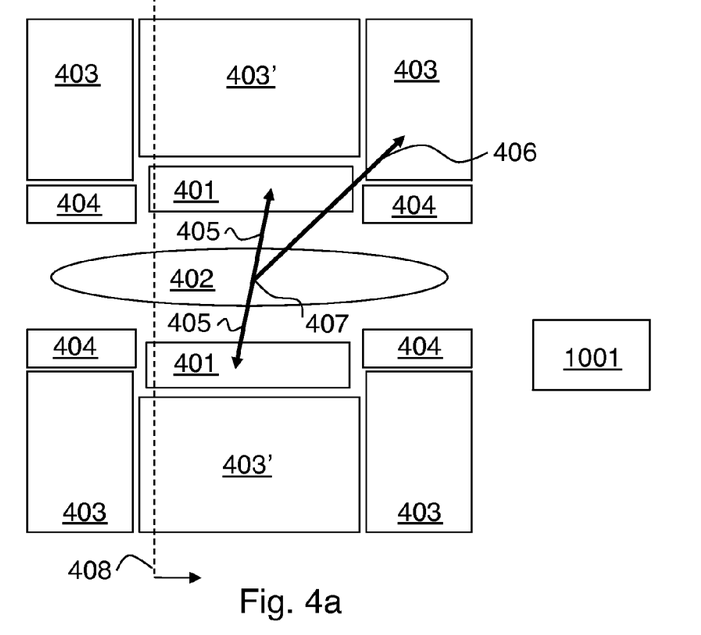
FIGS. 4a-b show a fourth embodiment of the invention.
Figure 4B:
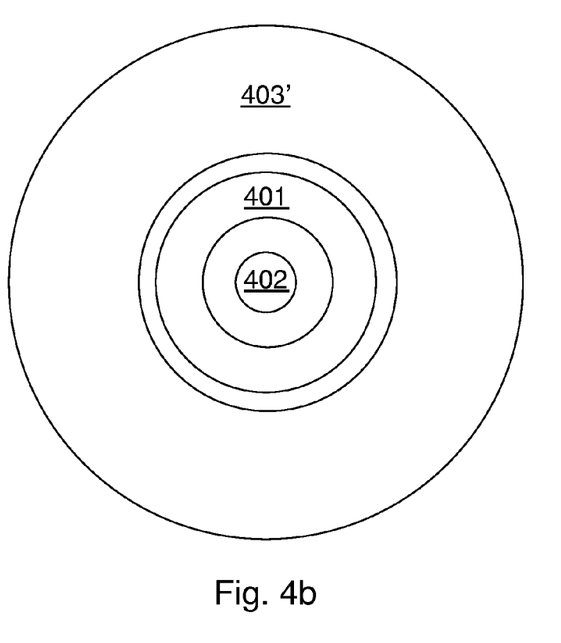

FIGS. 4a-b show a fourth embodiment of the invention, which is a second example of a whole body clinical PET system. Here FIG. 4b is an cross section view as seen from line 408. The apparatus for radiological imaging of FIGS. 4a-b includes an imaging positron emitting tomography (PET) detector array 401 capable of detecting and locating two-photon emission events resulting from positron annihilation to provide PET detector signals. Annihilation events occur in object 402 that is being imaged (e.g., a patient). The apparatus of FIG. 4a also includes one or more prompt gamma detectors 403 and 403', which are responsive to prompt gammas, and are not responsive to positron annihilation photons (at 511 keV). Thus the prompt gamma detectors are capable of improving the detection of a prompt gamma emission from isotopes that produce both a positron and a prompt gamma in cascade. FIG. 4a schematically shows such a 3-photon process, where an event at 407 leads to emission of a prompt gamma 406 and a positron (not shown) which annihilates to provide oppositely directed photons 405.

In this example, the prompt gamma detectors can be placed as an extra axial ring 403' adjacent to the conventional PET detector array 401. These extra prompt gamma detectors will increase the solid angle for capturing the third gamma rays emitted, and therefore increase the sensitivity for a triple coincidence detection. In addition to placing prompt gamma detectors 403' laterally around the PET detector array 401, prompt gamma detectors 403 can also be placed on both sides (axially) of the PET detector array 401. In this way, the PET detector array 401 can be substantially surrounded by prompt gamma ray detectors (403, 403') that are much more sensitive for gamma ray energies greater than 511 keV than just the conventional PET detector ring alone.

Optionally, shielding 404 for triple coincidence can be included to help reduce random coincidences from prompt gamma rays that are not from the imaging field of view. The materials used for such a shield 404 can include lead or tungsten to provide high stopping power. Using these shields 404, the prompt gamma rays can be physically collimated to reduce random coincidences.

In any of the preceding examples, some or all of the prompt gamma detectors can have an adjustable position. For example detectors 403 and/or 403' of the example of FIGS. 4a-b can have adjustable positions. Having adjustable detector positions can be helpful in various situations, e.g., to accommodate size differences in objects being imaged.

6) Experimental Example

Figure 5A:
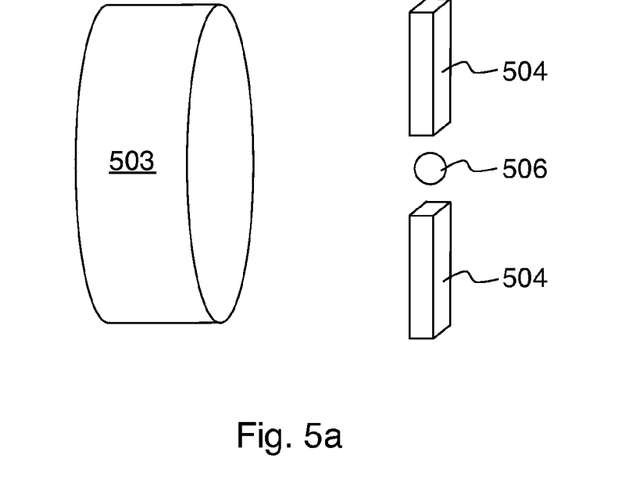
FIG. 5a shows an experimental configuration relating to principles of the invention.
Figure 5B:
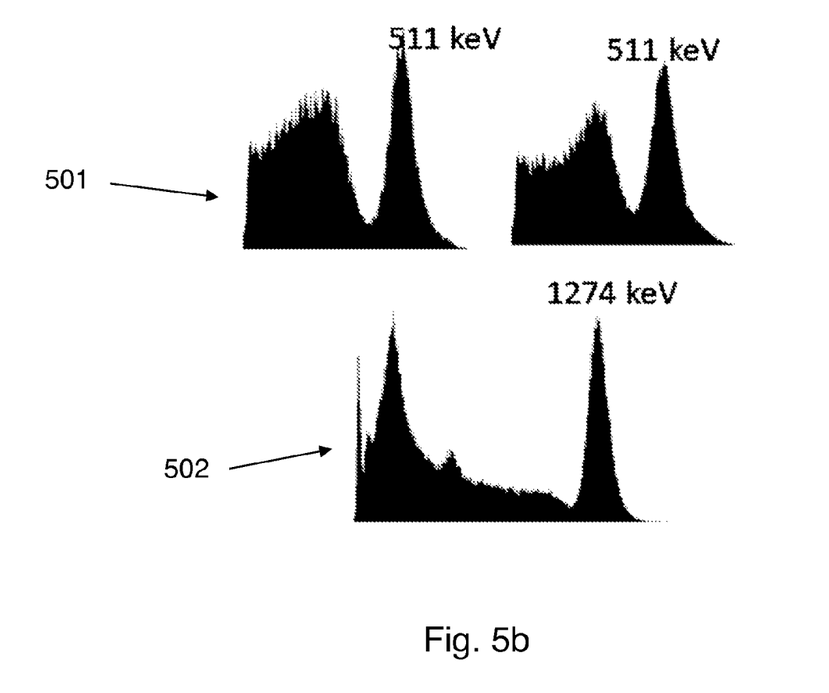

FIG. 5a shows an experimental configuration relating to principles of the invention. FIG. 5b shows results from the experiment of FIG. 5a. Here a source 506 including the prompt gamma emitter Na-22 is measured with two small detectors 504 (dimensions 3 mm by 3 mm by 20 mm) that are representative of PET detector array elements and a large detector 503 (radius 4 cm, height 4 cm) that is representative of the prompt gamma detector. The material for detectors 503 and 504 is LSO. Spectra 501 are from detectors 504, and spectrum 502 is from detector 503. The prompt gamma energy for Na-22 is 1274 keV, so it is apparent that detector 503 is responsive to the prompt gammas. It is also apparent that detector 503 can be made non-responsive to the 511 keV annihilation photons by appropriate energy gating. This experiment provides a proof of concept of one of the main advantages of the present approach—reduced cost.

Because the prompt gamma ray detector does not need to be spatially localizing, it can be much less complex and expensive (e.g., 503 on FIG. 5a) than a normal PET detector array. For example, a conventional clinical PET detector must resolve the annihilation photons by using many small crystals (e.g. 3 mm×3 mm×20 mm in dimension) that are readout by a very large number of expensive position-sensitive photodetectors such as photomultiplier (PMT) or silicon photomultiplier (SiPM) devices. In contrast, the prompt gamma detector can be made of a large bulk crystal. For example, in the case of a small animal PET scanner, the prompt gamma detector can be on the order of 8-20 cm in diameter by 5 cm thickness connected to a single photo-detector. Because no spatial localization is needed for the prompt gamma, the extra detector need not have the expensive crystal arrays and readout electronics of the spatially resolving PET detector array. Therefore, this approach of using prompt gamma ray detectors is significantly less complex and expensive than using a thicker or larger axial extent conventional PET ring to increase the sensitivity of triple coincident imaging.

7) Isotope Selection

Practice of the invention does not depend critically on the isotope that is used as the prompt gamma emitter. Any isotope that is consistent with the above-described principles can be employed.

The prompt gamma emitter may emit more than one gamma ray at different energies. Also, there may be a plurality of prompt gamma rays that are emitted in the decay cascade. The prompt gamma ray energy or energies only need to differ from 511 keV (the positron annihilation energy). Multiple prompt gamma emitters can be employed. For example, in multi-isotope imaging there may be isotopes A, B and C present. In this example, A can be a clean positron emitter and B and C can be triple coincident emitters where the energies of the prompt gamma rays from B and C are different and uniquely identifiable from each other.

Figure 6:
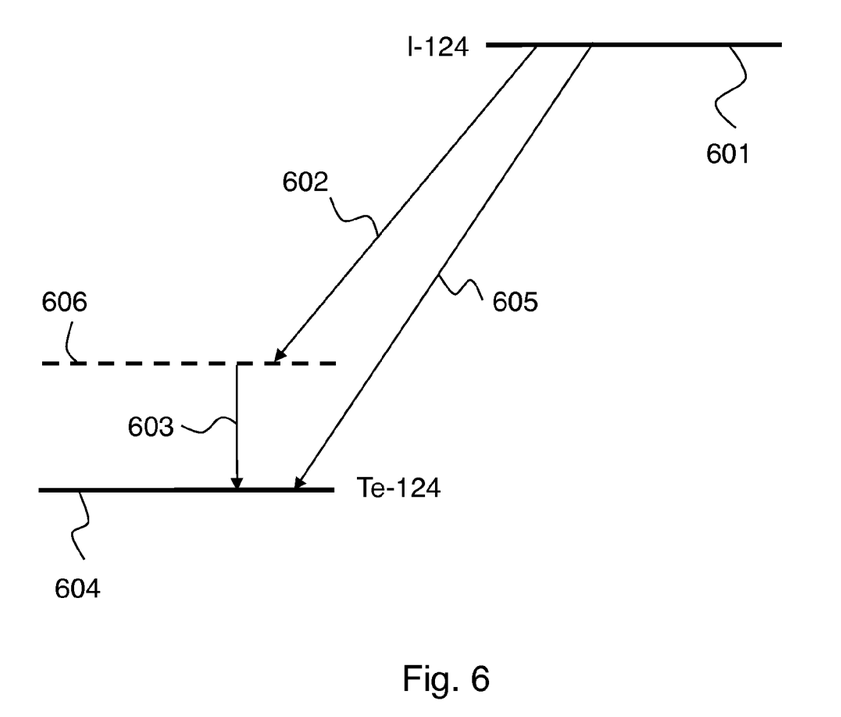
FIG. 6 shows a simplified nuclear energy level diagram for the transition from I-124 to Te-124.

Suitable isotopes include, but are not limited to: Sc-44, I-124, Ga-68, Na-22 and In-110. FIG. 6 shows a simplified nuclear energy level diagram for the transition from I-124 to Te-124. Here energy level 601 is the parent positron emitting isotope (i.e., I-124). Energy level 604 is the stable daughter isotope (i.e., Te-124). Energy level 606 is an intermediate state that can be reached by radioactive decay from state 601, and which can decay to state 604 via a decay process 603 of gamma ray emission (this gamma ray energy is about 0.6 MeV).

Decay process 602 can occur in two ways—positron emission (11.7%) and electron capture (25.1%). Similarly, decay process 605 can also occur in two ways—positron emission (10.8%) and electron capture (24.1%). These probabilities do not add up to 100% because numerous other transitions are omitted from this figure for simplicity. Electron capture processes lead to emission of a gamma ray, but no positron is emitted.

In cases where decay process 602 is via positron emission, a prompt gamma can also be emitted via process 603. This is an example of the 3-photon events considered above. If I-124 decays via positron emission in process 605, there is no prompt gamma. Thus, some of the positron emissions from I-124 lead to 3-photon events, and others lead to 2-photon events. Processor 1001 can use calibration algorithms to correct for these different decay probabilities.

The preceding description has been by way of example as opposed to limitation, so the invention can also be practiced via numerous variations of the given examples. The position, number, geometry, material composition, and dimensions of both the extra prompt gamma detectors and shielding (if present) can all be varied as needed for system design.

The invention claimed is:

1. Apparatus for radiological imaging, the apparatus comprising:
    an imaging positron emitting tomography (PET) detector array capable of detecting and locating two-photon emission events resulting from positron annihilation to provide PET detector signals;
    one or more prompt gamma detectors responsive to a prompt gamma ray from isotopes that produce both a positron and a prompt gamma ray in cascade, wherein the prompt gamma detectors are not responsive to positron annihilation photons; and
    a processor coupled to the imaging PET detector array and to the prompt gamma detectors and configured to provide a classification of the PET detector signals as 2-photon events or as 3-photon events according to signals provided by the PET detector array and by the prompt gamma detectors;
    wherein an object being imaged by the apparatus for radiological imaging includes at least a first radio-isotope that provides two-photon emission events without associated prompt gamma rays and a second radio-isotope that provides two-photon emission events with associated prompt gamma rays;
    wherein the apparatus is configured to simultaneously and independently image the object with the first and second radio-isotopes according to the classification of the PET detector signals as 2-photon events or as 3-photon events.

2. The apparatus of claim 1, wherein the apparatus for radiological imaging is a whole body PET system, a small animal PET system, or an application-specific PET system.

3. The apparatus of claim 1, wherein the PET detector array is disposed to laterally enclose an object being imaged.

4. The apparatus of claim 3, wherein the prompt gamma detectors comprise a first prompt gamma detector and a second prompt gamma detector, wherein the first and second prompt gamma detectors longitudinally enclose the object being imaged.

5. The apparatus of claim 4, wherein the prompt gamma detectors further comprise one or more third prompt gamma detectors disposed laterally around the PET detector array.

6. The apparatus of claim 3, wherein the prompt gamma detectors comprise one or more prompt gamma detectors disposed laterally around the PET detector array.

7. The apparatus of claim 1, wherein at least one of the prompt gamma detectors has an adjustable position.

8. The apparatus of claim 1, wherein the PET detector array is configured to provide a spatial resolution substantially more precise than a size of the PET detector array.

9. The apparatus of claim 1, wherein the prompt gamma detectors do not provide a spatial resolution more precise than a size of the prompt gamma detectors.

10. The apparatus of claim 1, wherein the apparatus is configured for use with a triple-coincidence isotope selected from the group consisting of: Sc-44, I-124, Ga-68, Na-22 and In-110.

11. The apparatus of claim 1, wherein the apparatus for radiological imaging is a whole body PET system, wherein w is a patient width and c is the speed of light, wherein $\tau=w/c$, and wherein the apparatus is configured to use a triple-coincidence isotope having a time difference T between positron emission and prompt gamma emission such that T is less than about $\tau$.

12. The apparatus of claim 1, wherein the apparatus for radiological imaging is a small animal or application specific PET system, wherein $T_{FWHM}$ is a detector time response full width half-maximum, and wherein the apparatus is configured to use a triple-coincidence isotope having a time difference T between positron emission and prompt gamma emission such that T is less than about $2T_{FWHM}$.

13. The apparatus of claim 1, wherein the prompt gamma detector does not provide spatial localization upon detection of the prompt gamma ray.

* * * * *